United States Patent [19]

Thompson

[11] Patent Number: 5,385,557
[45] Date of Patent: Jan. 31, 1995

[54] SHIELDING DEVICE FOR A SYRINGE NEEDLE

[76] Inventor: Clarence J. Thompson, P.O. Box 4338, Oneida, Tenn. 37841

[21] Appl. No.: 222,025

[22] Filed: Apr. 4, 1994

[51] Int. Cl.⁶ .............................................. A61M 5/32
[52] U.S. Cl. ..................................... 604/198; 604/263
[58] Field of Search ............... 604/110, 192, 187, 198, 604/263, 218, 230

[56] References Cited

U.S. PATENT DOCUMENTS

| | | |
|---|---|---|
| 2,571,653 | 10/1951 | Bastien . |
| 3,943,927 | 3/1976 | Norgren . |
| 4,356,822 | 11/1982 | Winstead-Hall . |
| 4,631,057 | 12/1986 | Mitchell . |
| 4,826,491 | 5/1989 | Schramm . |
| 4,955,868 | 9/1990 | Klein . |
| 5,084,030 | 1/1992 | Byrne et al. . |
| 5,106,380 | 4/1992 | Lobello . |
| 5,998,920 | 3/1991 | Johnson . |

FOREIGN PATENT DOCUMENTS

| | | |
|---|---|---|
| 704152 | 4/1966 | Italy . |
| 2202747A | 10/1988 | United Kingdom . |

*Primary Examiner*—John D. Yasko
*Attorney, Agent, or Firm*—Richard C. Litman

[57] ABSTRACT

A retractable needle shielding device for use with a medical syringe is devised to reduce the risk of inadvertent needle strikes. The shield includes a retractable tubular body movable from a position completely shielding the needle to a position where the needle extends outward from the tubular body. The tubular body may be configured to retract over the barrel of the syringe and, in which case, should be formed of a substantially transparent material. The shield may include a collar engageable in series with and in fluid communication with the nose of the barrel and the hub of the needle. The collar preferably includes radially extending guides which are engageable with grooves disposed interiorly of the tubular body. The collar may be substantially the same length as the tubular body and, therefore, not retract over the syringe barrel. Frictional elements are provided to resist the displacement of the tubular body relative to the syringe. The tubular body is dimensioned and configured to be extensible over the length of a syringe needle and the needle cap.

8 Claims, 3 Drawing Sheets

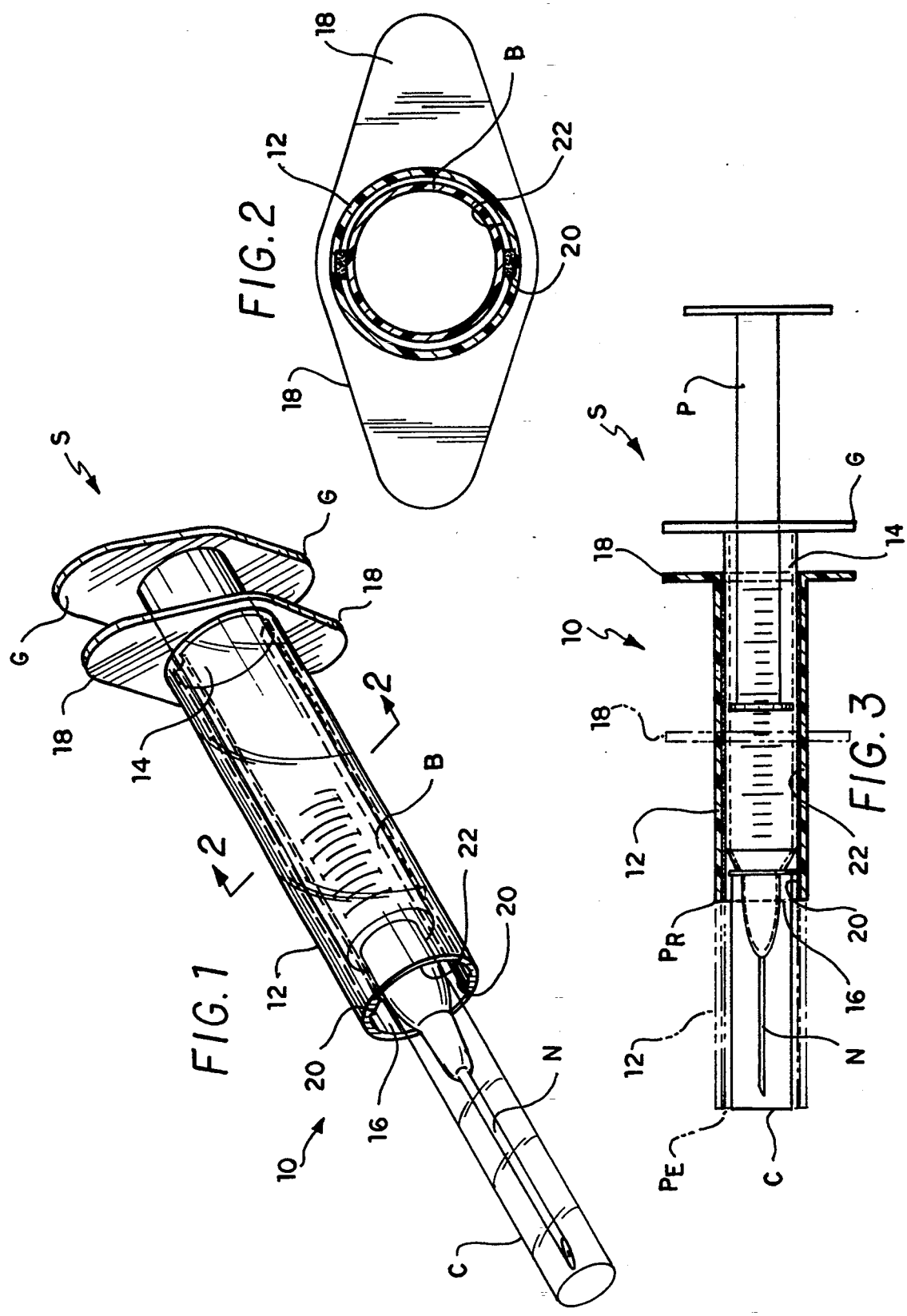

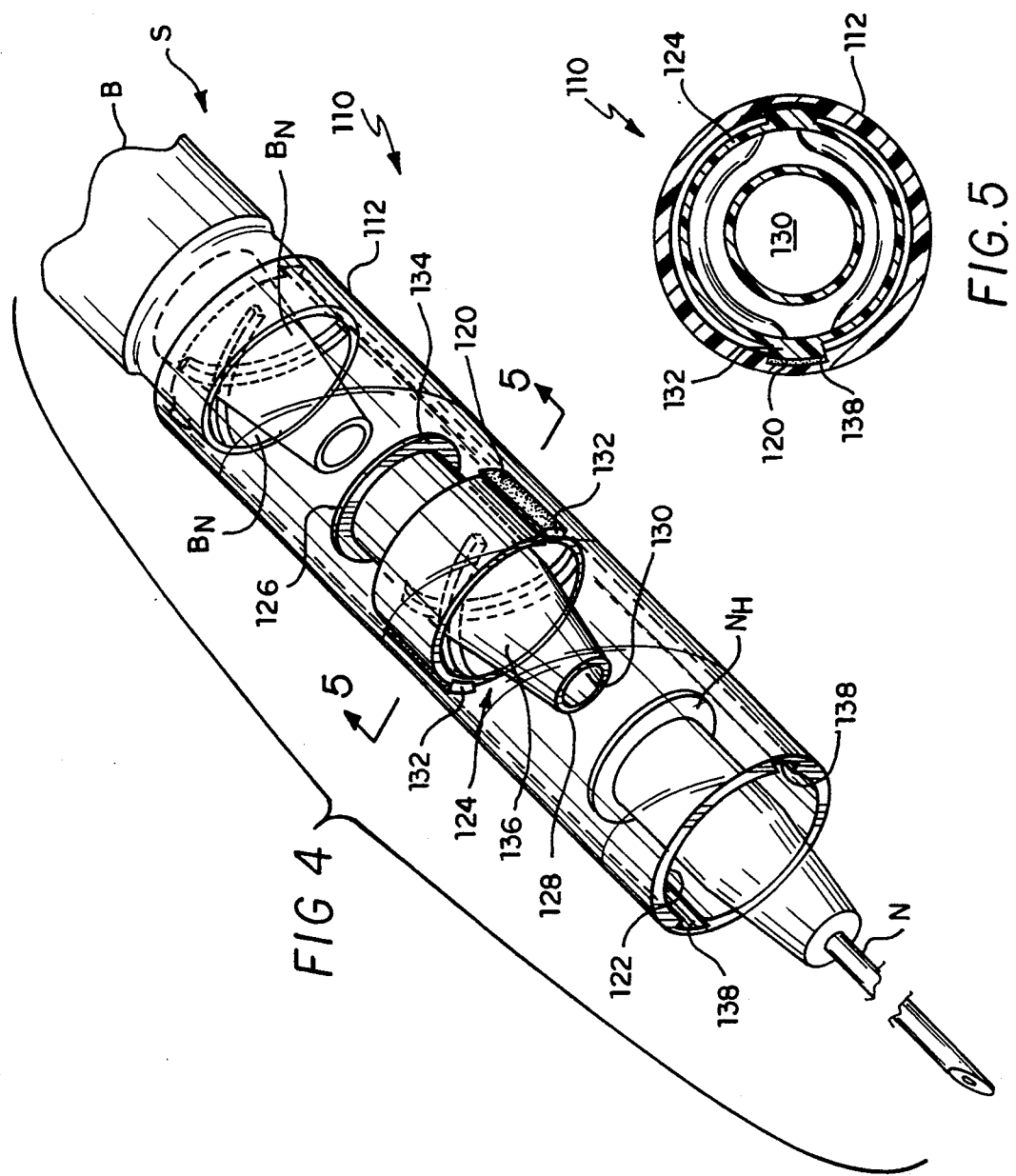

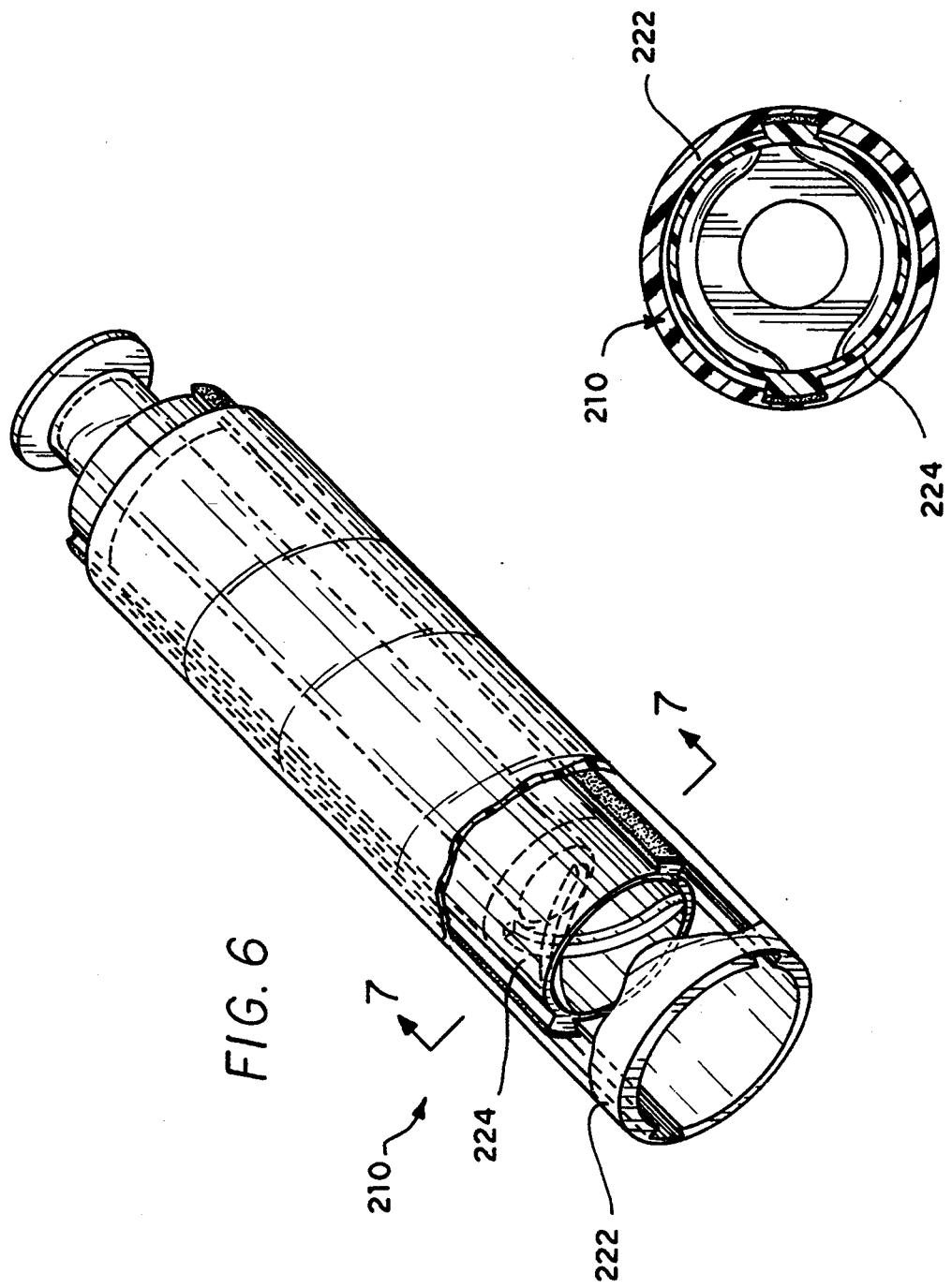

SHIELDING DEVICE FOR A SYRINGE NEEDLE

BACKGROUND OF THE INVENTION

1. Field of the Invention

The present invention relates generally to a needle shielding device for use in reducing the risk of inadvertent needle strikes of both a patient and a person administering an injection or drawing blood from the patient.

2. Description of the Prior Art

Medical professionals are susceptible to accidental needle strikes during the administration of medicines to, or when drawing blood from, a patient. There exists an increasing concern for the potential transmission of infectious diseases, such as AIDS and hepatitis, through exposure to accidental needle strikes. To combat the spread of disease, there have been numerous attempts to devise needle shielding devices intended to reduce the risk of accidental needle strikes. For example, a sheath is disclosed in U.S. Pat. No. 2,571,653, issued Oct. 16, 1951 to Victor G. Bastien. The sheath is operable between an extended position and a retracted position, and is cooperatively engageable with the barrel of a syringe to lock in each position. An annular opening is provided at each end of the sheath. When the sheath is in the retracted position, the needle is extendable through one opening and the barrel is received by the other opening.

Another needle shielding device is shown in U.S. Pat. No. 4,356,822, issued Nov. 2, 1982 to Deborah Winstead-Hall. Winstead-Hall discloses a cap which receives at least a portion of the barrel of a syringe. The cap includes locking members for securing the cap and barrel in a number of relative positions.

U.S. Pat. No. 4,631,057, issued Dec. 23, 1986 to Charles B. Mitchell, discloses yet another needle shielding device. This needle shield device is mounted on the barrel of a syringe and is movable relative to the barrel from a retracted position to an extended position. An annular rib engages the barrel to maintain the shielding device in a retracted position. Upon extension of the shielding device, a pair of teeth engage the barrel to lock the shield in an extended position.

A shielding device is disclosed in U.S. Pat. No. 4,826,491, issued May 2, 1989 to James J. Schramm, wherein the shield includes teeth which cooperate with a syringe to provide three distinct retaining positions. The shield is substantially non-releasable from an extended position around the needle.

U.S. Pat. No. 4,955,868, issued Sep. 11, 1990 to Edward Klein, relates to a modification of a hypodermic syringe having a shield to cover the needle of the syringe. This shield is retractable to allow the needle to extend past the shield. A spring is used to automatically return the shield to a position covering the needle.

Shielding devices for adaptation to conventional syringes are disclosed in U.S. Pat. No. 4,998,920, issued Mar. 12, 1991 to Delores Johnson, and U.S. Pat. No. 5,106,380, issued Apr. 21, 1992 to Diane Lobello. These devices each include a collar adapted to be affixed to a syringe adjacent the syringe needle and a sleeve adapted to be arranged circumjacent the syringe barrel. These sleeves engage the collar upon placement of the sleeve in an extended position. The sleeve according to Johnson is further engageable with the collar in a retracted position.

Another shielding device for use with syringes is disclosed in U.S. Pat. No. 5,084,030, issued Jan. 28, 1992 to Phillip O. Byrne et al. The shield according to Byrne is movable from a retracted position to an extended position and is maintained in the extended position by a hidden projection that engages the syringe.

UK Patent Application GB 2 202 747 A, published Oct. 5, 1988 for William Ducat, discloses a needle shield which includes a sleeve that is axially slidable over the barrel of a syringe. The sleeve may be spring biased and lockable in position. Another needle shielding device deemed of interest is shown in an Italian publication, No. 704152, published Apr. 19, 1966 for Unberto Fonghini.

None of the above inventions and patents, taken either singly or in combination, is seen to describe the instant invention as claimed.

SUMMARY OF THE INVENTION

The present invention relates to a retractable needle shielding device for use with a medical syringe. This device shields the needle to reduce the risk of inadvertent needle strikes to both a patient and a person administering an injection to, or drawing blood from, the patient. The shield includes a retractable tubular body movable from a position completely shielding the needle to a position where the needle extends outward from the tubular body.

In a first embodiment, the tubular body is retractable over the barrel of the syringe. For at least this reason, the tubular member should be constructed from a substantially transparent material to permit markings on the syringe to be visually observed therethrough.

In a second and third embodiment, the shield includes a collar engageable in series with the barrel nose and the needle hub. These collars each include radially extending guides which are engageable with grooves disposed interiorly of their respective tubular bodies. The cooperative engagement of the guides and grooves prevents each of the tubular bodies from rotating with respect to its respective collar. This enables each collar to be threadably engaged with the needle hub by rotating the tubular body.

The tubular body, in accordance with the second and third embodiments, is retractable over its respective collar. The collar, according to the second embodiment, has a significantly smaller length than that of the tubular body. For at least this reason, the tubular body according to the second embodiment, similar to that of the first embodiment, is retractable over the barrel. Hence, this tubular body should be likewise be fabricated from a substantially transparent material.

The collar according to the third embodiment is substantially the same length as the tubular body. Therefore, unlike the first and second embodiments, the tubular body according to the third embodiment does not retract over the syringe barrel. It follows that it need not be made of a transparent material. Further, since the tubular body of this embodiment does not retract over the syringe barrel, the tubular body need not have a cross-section larger than that of the syringe barrel and therefore, is not limited in its use to syringes having smaller cross-sections.

In each of the aforementioned embodiments, a frictional element is provided to resist the displacement of the tubular body relative to the syringe. In the first embodiment, this frictional element in affixed to the interior surface of the tubular body. In the second and third embodiments, a plurality of frictional elements are affixed to the radial extremities of their respective collars. The frictional element, according to at least the first embodiment, is preferably substantially transparent so as to not interfere with a visual observation therethrough.

The frictional elements resist movement of the tubular bodies. Hence, the tubular bodies must be purposefully manipulated by the medical professional. To this end, the frictional elements eliminate the need for catches and the like.

In all three embodiments, the tubular body is extensible over the entire length of a syringe needle. It should be noted that a biasing element may be provided to displace the tubular body to an extended position where the tubular body conceals the needle.

Accordingly, it is a principal object of the invention to provide a needle shielding device capable of frictionally engaging syringe assemblies.

It is another object that the device be easily and readily displaceable while inserting a needle into, or extracting a needle from, a medicine vial or a patient.

It is a further object that the shield be dimensioned and configured to cover a syringe needle and receive a needle cap when capping the needle.

Still another object that the shielding device lessen the possibility of spreading contaminants through the use of a common syringe.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is an environmental perspective view of a needle shielding device according to the present invention.

FIG. 2 is an enlarged scale, cross-sectional view drawn along lines 2—2 of FIG. 1.

FIG. 3 is a reduced scale, elevational view of the needle shielding device shown in FIG. 1.

FIG. 4 is an enlarged scale, environmental perspective view of an alternative needle shielding device.

FIG. 5 is cross-sectional view drawn along lines 5—5 of FIG. 4.

FIG. 6 is a partially cutaway, environmental perspective view of another needle shielding device.

FIG. 7 is an enlarged scale, cross-sectional view drawn along lines 7—7 of FIG. 6.

Similar reference characters denote corresponding features consistently throughout the attached drawings.

DETAILED DESCRIPTION OF THE PREFERRED EMBODIMENTS

The present invention, as is shown in FIGS. 1 through 3, is a needle shielding device 10. The shielding device 10 is intended for use in offering protection against inadvertent puncture of both a patient and a person administering the injection or drawing blood from the patient.

The shielding device 10 includes a tubular body 12 preferably formed of a hardened rubber or plastic material. The tubular body 12 is further dimensioned to loosely receive the barrel B of a syringe S. For example, the tubular body 12 shown has a cross-section complementary in shape and slightly larger than that of the syringe barrel B. A first open end 14 is provided through which the barrel B is received, and a second open end 16 is provided through which the syringe needle N may extend. The tubular body 12 is telescopically and axially displaceable over a barrel B between an extended position $P_E$ and a retracted position $P_R$ to respectively conceal and expose the needle N. It should be noted that the tubular body 12 should be substantially transparent to enable the barrel B to be visually observed therethrough.

End formations 18 may be provided at the first end 14 of the tubular body 12. The dimensions of the end formations 18 may be slightly larger than that of the syringe finger grips G to improve the maneuverability of the tubular body 12 relative to the syringe S.

Frictional elements, such as the frictional strips 20 shown, are located intermediate the tubular body 12 and the syringe S. Preferably, the frictional strips 20 are affixed to the interior surface 22 of the tubular body 12. The strips 20 are preferably diametrically spaced apart and extend longitudinally the full extent of the tubular body 12. The strips 20 are intended to frictionally engage the outer wall of the barrel B offering resistance to an axial displacement of said tubular body 12 relative to the syringe S.

The shielding device 10 according to this embodiment may be dimensioned and configured to retrofit existing syringes S and does not interfere with the needle N, the needle cap C, or the operation of the syringe plunger P.

It should be noted that, although two frictional strips are shown, as few as one and more than two frictional strips 20 may be affixed to the inner wall 22 of the tubular body 12. To provide an equal distribution of frictional engagement about the barrel B and between the tubular body 12 and the barrel B, the frictional strips 20 should be spaced equidistantly apart. For example, placing the two frictional strips 20 diametrically apart, as is shown, provides an equal distribution of friction about the barrel B and between the barrel B and the tubular body 12 and therefore, further reduces the risk of the needle shielding device 10 being inadvertently displaced.

In a second embodiment, as is shown in FIGS. 4 and 5, the needle shielding device 110 includes a collar 124. The collar 124 has a first end 126 and second end 128 opposite the first end 126. The first end 126 is configured to be matingly engageable with the nose $B_N$ of the barrel B. The second end 128 is configured to be matingly engageable with the hub $N_H$ of the needle N. In this way, the collar 124 is located in series with the barrel B and the needle N.

The collar 124 has a bore 130 passing therethrough which is in fluid communication with a bore in the nose $B_N$ of the barrel B and a bore in the hub $N_H$ of the needle N. This provides a passage for fluid to flow through the collar 124 from the nose $B_N$ to the hub $N_H$. For at least this reason, the collar 124 should be fabricated from a sterile material, such as a material similar to that of which the syringe S is fabricated.

The collar 124 should further be configured to sealingly engage the nose $B_H$ of the barrel B as well as the hub $N_H$ of needle N to prevent leakage of fluid therefrom. This may be accomplished through the formation of a LUER LOCK configuration 134 at the first end 126 of the collar 124 which is engageable with the nose $B_N$ of the barrel B and through the formation of a LUER LOCK configuration 136 at the second end 128 of the collar 124 which is engageable with the hub $N_H$ of the needle N.

The collar 124 further includes diametrically opposed, radially extending guide members 132. The radial extremities of the guide members 132 are each provided with a frictional element, such as the elongated frictional strips 120 shown.

These guides 132 communicate with longitudinally extending grooves 138 disposed within the inner wall 122 of the tubular body 112. The grooves 138, like the guides 132, are diametrically opposed. The grooves 138 are further configured to possess a shape complementary to that of the guides 132. The guides 132 restrict the displacement of the tubular body 112 relative to the collar 124 to an axial displacement.

The frictional strips 120 each engage a respective groove 138. A tight fit relationship exists between each frictional strip 120 and a respective one of the grooves 138 to increase the resistance to the axial displacement of the tubular body 112 relative to the collar 124 and, in turn, relative to the syringe S.

In a third embodiment, as shown in FIGS. 6 and 7, the needle shielding element or device 210 includes a collar 224 having an extension substantially equivalent to that of the tubular body 222. Unlike the first two embodiments, according to this embodiment, the tubular body 222, when retracted, does not overlap the syringe S (not shown) but overlaps the collar 224. For this reason, the tubular body 222 need not be dimensioned to receive the barrel B (not shown), but may have a cross-section smaller than that of the barrel B. Since the tubular body 222 does not retract over the barrel B, the barrel B remains fully exposed for visual observation when the needle shielding device 210 is retracted to expose the needle N (not shown).

In the second and third embodiments, as are shown in FIGS. 4 through 7, after the syringe S has been used, the collar 124, 224 with the needle N attached thereto may be removed from the nose $B_N$ of the barrel B by rotating the tubular body 112, 222. This enables the needle N and the shielding device 110, 210 thereabout to be discarded independently of the barrel B.

In each embodiment, the tubular bodies 12, 112, 222, as shown in FIGS. 1 through 7, are each dimensioned to entirely enshroud a needle N and to extend beyond the extent of the needle N, totally protecting a medical professional and a patient from inadvertent needle pricks. The tubular bodies 12, 112, 222 are further each dimensioned and configured to cover the needle N and receive a needle cap C when capping the needle N while the tubular bodies 12, 112, 222 are each fully extended.

It is to be understood that the present invention is not limited to the embodiments described above, but encompasses any and all embodiments within the scope of the following claims.

I claim:

1. A needle guard for use with a syringe comprising:
   a tubular body having a cross-section complementary in shape and slightly larger than that of the syringe, said tubular body being axially displaceable between an extended position and a retracted position to respectively conceal and expose a needle of the syringe;
   a first frictional element offering resistance to an axial displacement of said tubular body relative to the syringe;
   a collar having a first end and a second end, said first end being configured to be matingly engageable with a nose of a barrel of the syringe, said second end being configured to be matingly engageable with a hub of the needle of the syringe;
   said collar including a bore passing therethrough, said bore being in fluid communication with the bore in the nose of the barrel and the bore in the hub of the needle;
   said collar being configured to sealingly engage the nose of the barrel and the hub of the needle to prevent leakage of fluid therefrom; and
   said first frictional element being affixed to an exterior surface of said collar.

2. A needle guard according to claim 1, wherein said tubular body includes a first open end and a second open end opposite said first open end, said tubular body being dimensioned and configured to loosely receive the syringe through said first open end thereof, said tubular body further being dimensioned and configured to be telescopically slidable axially over the syringe between the extended position and the retracted position, said second open end being dimensioned to enable the needle of the syringe to extend therethrough upon sliding said tubular body to the retracted position.

3. A needle guard according to claim 1, wherein said collar is fabricated from a sterile plastic material.

4. A needle guard according to claim 1, further including a second frictional element, and wherein
   said collar further includes diametrically opposed, radially extending guide members, each one of said frictional elements being affixed to a radial extremity of a respective one of said guide members, and wherein
   said tubular body further includes diametrically opposed, longitudinally extending grooves disposed interiorly of the tubular body, said grooves being configured to a shape complementary to that of said guides,
   said guides slidably communicating with a respective one of said grooves.

5. A needle guard according to claim 1, wherein said collar is fabricated from a sterile plastic material.

6. A needle guard according to claim 1, further including a second frictional element, and wherein
   said collar further includes diametrically opposed, radially extending guide members, each one of said frictional elements being affixed to a radial extremity of a respective one of said guide members, and wherein
   said tubular body further includes diametrically opposed, longitudinally extending grooves disposed interiorly of the tubular body, said grooves being configured to a shape complementary to that of said guides,
   said guides slidably communicating with a respective one of said grooves.

7. A needle guard according to claim 1, wherein said tubular body has a length substantially smaller than that of said collar, such that upon displacment of said tubular body to the retracted position, said tubular body telescopically slides axially over the syringe.

8. A needle guard for use with a syringe comprising:
   a tubular body having a first open end and a second open end opposite said first open end, said tubular body being dimensioned and configured to loosely receive the syringe through said first open end thereof, said tubular body further being dimensioned and configured to be telescopically slidable axially over the syringe between an extended position and a retracted position, said second open end being dimensioned to enable the needle of the syringe to extend therethrough upon sliding said tubular body to the retracted position;

a frictional element intermediate said tubular body and the syringe, said frictional element offering resistance to an axial displacement of said tubular body relative to the syringe;

a collar having a first end and a second end, said first end being configured to be matingly engageable with a nose of a barrel of the syringe, said second end being configured to be matingly engageable with a hub of a needle of the syringe, said collar including a bore passing therethrough, said bore being in fluid communication with the bore in the nose of the barrel and the bore in the hub of the needle, said collar being configured to sealingly engage the nose of the barrel and the hub of the needle to prevent leakage of fluid therefrom, and said frictional element being affixed to an exterior surface of said collar.

* * * * *